United States Patent
Hill et al.

(10) Patent No.: US 12,257,105 B2
(45) Date of Patent: Mar. 25, 2025

(54) SYSTEM FOR TRACKING AND IMAGING A TREATMENT PROBE

(71) Applicant: Covidien LP, Mansfield, MA (US)

(72) Inventors: Morgan L. Hill, Conifer, CO (US);
Eric W. Larson, Lakewood, CO (US);
Casey M. Ladtkow, Erie, CO (US);
Nikhil P. Mankar, Pune (IN); Arlen J. Reschke, Longmont, CO (US);
Jeetendra Bharadwaj, Erie, CO (US);
Robert J. Behnke, II, Erie, CO (US);
William J. Dickhans, Longmont, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/474,431

(22) Filed: Sep. 26, 2023

(65) Prior Publication Data
US 2024/0008846 A1    Jan. 11, 2024

Related U.S. Application Data

(63) Continuation of application No. 16/951,194, filed on Nov. 18, 2020, now Pat. No. 11,771,401, which is a
(Continued)

(51) Int. Cl.
*A61B 8/00* (2006.01)
*A61B 8/08* (2006.01)
(Continued)

(52) U.S. Cl.
CPC .......... *A61B 8/4254* (2013.01); *A61B 8/0841* (2013.01); *A61B 8/085* (2013.01);
(Continued)

(58) Field of Classification Search
CPC ..... A61B 8/4254; A61B 8/0841; A61B 8/085; A61B 8/12; A61B 8/4444; A61B 34/20; A61B 2034/2051
See application file for complete search history.

(56) References Cited

U.S. PATENT DOCUMENTS

| | | | |
|---|---|---|---|
| 3,868,565 A | 2/1975 | Kuipers | |
| 3,983,474 A | 9/1976 | Kuipers | |

(Continued)

FOREIGN PATENT DOCUMENTS

| | | |
|---|---|---|
| CN | 101569556 A | 11/2009 |
| CN | 102525558 A | 7/2012 |

(Continued)

OTHER PUBLICATIONS

"Hypotube Definition," Jul. 27, 2014, Modern Grinding <http://www.moderngrinding.com/hypotube-definition.php>.
(Continued)

*Primary Examiner* — Joseph M Santos Rodriguez
*Assistant Examiner* — Zainab Mohammed Aldarraji
(74) *Attorney, Agent, or Firm* — Carter, DeLuca & Farrell LLP

(57) ABSTRACT

A system includes a treatment probe, a first tracking sensor configured to track a location of the treatment probe, an ultrasound imager, a second tracking sensor configured to track a location of the ultrasound imager, and a tracking system. The ultrasound imager generates real-time ultrasound images. The tracking system receives location information from the first and second tracking sensors, tracks the location of the treatment probe and the location of the ultrasound imager, and displays the real-time ultrasound images and a representation of the treatment probe in one or more pre-stored images.

20 Claims, 8 Drawing Sheets

Related U.S. Application Data continuation of application No. 14/930,900, filed on Nov. 3, 2015, now Pat. No. 10,869,650.

(60) Provisional application No. 62/076,132, filed on Nov. 6, 2014.

(51) Int. Cl.
*A61B 8/12* (2006.01)
*A61B 34/20* (2016.01)

(52) U.S. Cl.
CPC .............. *A61B 8/12* (2013.01); *A61B 8/4444* (2013.01); *A61B 34/20* (2016.02); *A61B 2034/2051* (2016.02)

(56) References Cited

U.S. PATENT DOCUMENTS

| | | | |
|---|---|---|---|
| 4,017,858 A | 4/1977 | Kuipers | |
| 4,054,881 A | 10/1977 | Raab | |
| 4,287,809 A | 9/1981 | Egli et al. | |
| 4,314,251 A | 2/1982 | Raab | |
| 4,328,548 A | 5/1982 | Crow et al. | |
| 4,346,384 A | 8/1982 | Raab | |
| 4,394,831 A | 7/1983 | Egli et al. | |
| 4,396,885 A | 8/1983 | Constant | |
| 4,582,066 A | 4/1986 | Barnes | |
| 4,613,866 A | 9/1986 | Blood | |
| 4,710,708 A | 12/1987 | Rorden et al. | |
| 4,737,794 A | 4/1988 | Jones | |
| 4,742,356 A | 5/1988 | Kuipers | |
| 4,849,692 A | 7/1989 | Blood | |
| 4,877,033 A | 10/1989 | Seitz, Jr. | |
| 5,307,072 A | 4/1994 | Jones, Jr. | |
| 5,377,678 A | 1/1995 | Dumoulin et al. | |
| 5,503,154 A | 4/1996 | Belef | |
| 5,600,330 A | 2/1997 | Blood | |
| 5,646,525 A | 7/1997 | Gilboa | |
| 5,729,129 A | 3/1998 | Acker | |
| 5,752,513 A | 5/1998 | Acker et al. | |
| 5,993,437 A | 11/1999 | Raoz | |
| 6,375,615 B1 | 4/2002 | Flaherty et al. | |
| 6,615,155 B2 | 9/2003 | Gilboa | |
| 6,695,772 B1 | 2/2004 | Bon | |
| 10,869,650 B2 | 12/2020 | Hill et al. | |
| 11,771,401 B2 | 10/2023 | Hill et al. | |
| 2002/0107445 A1 | 8/2002 | Govari | |
| 2004/0049111 A1 | 3/2004 | Hirooka | |
| 2004/0254458 A1 | 12/2004 | Govari | |
| 2005/0090742 A1 | 4/2005 | Mine et al. | |
| 2007/0167787 A1 | 7/2007 | Glossop | |
| 2009/0266957 A1 | 10/2009 | Cermak | |
| 2009/0275833 A1 | 11/2009 | Ikeda | |
| 2010/0081920 A1 | 4/2010 | Whitmore, III et al. | |
| 2010/0298704 A1 | 11/2010 | Pelissier et al. | |
| 2012/0143055 A1 | 6/2012 | Ng et al. | |
| 2014/0046315 A1 | 2/2014 | Ladtkow et al. | |
| 2014/0081659 A1 | 3/2014 | Nawana | |
| 2014/0121502 A1 | 5/2014 | Vignon et al. | |
| 2017/0319174 A1 | 11/2017 | Hill | |

FOREIGN PATENT DOCUMENTS

| | | |
|---|---|---|
| EP | 0922966 A2 | 6/1999 |
| JP | 2005058584 A | 3/2005 |
| KR | 20160064574 A | 6/2016 |
| WO | 9404938 A1 | 3/1994 |
| WO | 9605768 A1 | 2/1996 |
| WO | 99/32033 A1 | 7/1999 |

OTHER PUBLICATIONS

"Oxy Clip Cylinder Holder," Nov. 1, 2013, Ferno <http://www.fernoems.com/en/powerflexx/Oxy-Clip-Cylinder-Holder.aspx&g-t.

"New Hypotube for PTCA Catheters launched," Feb. 1, 2006, Creganna Medical Devices <http://www.creganna.com/new-hypotube-for-ptca-catheters-launc-hed/>.

The International Search Report for corresponding application No. PCT/US2015/05911, dated Jan. 26, 2016, 2 pages.

Extended European Search Report dated Jul. 5, 2018 in corresponding European Patent Application No. 15856682.

Notice of Reasons for Rejection issued by the Japanese Patent Office dated Feb. 18, 2019 in corresponding Japanese Patent Application No. 2017-523440, with English translation.

Australian Examination Report issued in corresponding Appl. No. AU 2015342868 dated Jul. 2, 2019 (3 pages).

Chinese Office Action issued in corresponding Appl. No. CN 201580061112.0 dated Jun. 21, 2019, together with English language translation (19 pages).

Notice of Reasons for Rejection issued by the Japanese Patent Office dated May 16, 2019 in corresponding Japanese Patent Application No. 2017-523440 with English language translation.

European Communication pursuant to Article 94(3) EPC issued in corresponding Appl. No. EP 15856382.8 dated Aug. 8, 2019 (4 pages).

Examination Report issued in corresponding application EP 15856682.8 dated Aug. 12, 2021 (4 pages).

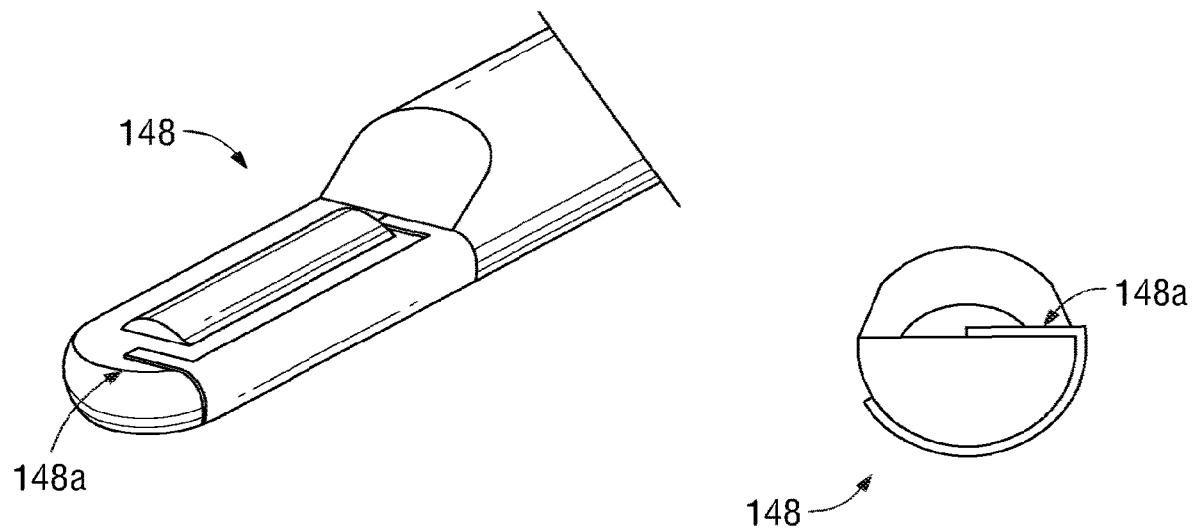
FIG. 4E
FIG. 4F
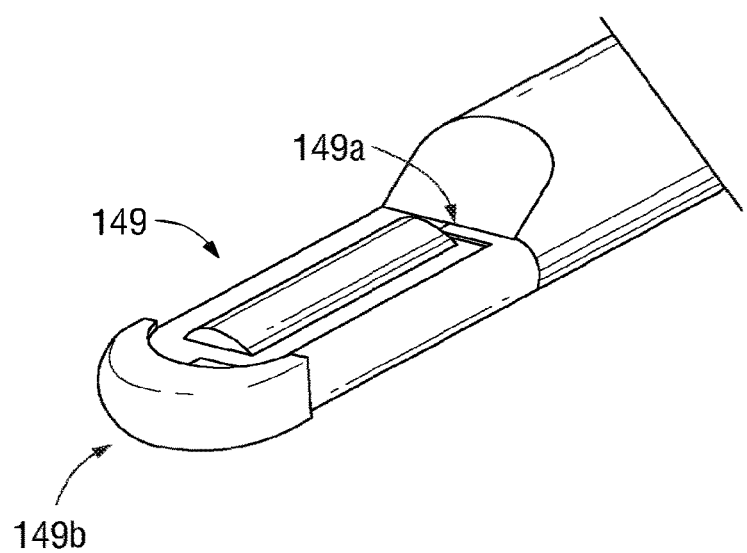
FIG. 4G

SYSTEM FOR TRACKING AND IMAGING A TREATMENT PROBE

CROSS-REFERENCE TO RELATED APPLICATIONS

This application is a continuation of U.S. patent application Ser. No. 16/951,194, filed on Nov. 18, 2020, now U.S. Pat. No. 11,771,401, which is a continuation of U.S. patent application Ser. No. 14/930,900, filed on Nov. 3, 2015, now U.S. Pat. No. 10,869,650, which claims the benefit of the filing date of provisional U.S. Patent Application No. 62/076,132, filed on Nov. 6, 2014.

FIELD

The present disclosure relates to systems and devices for a tracking and treatment. More particularly, the present disclosure relates to systems for tracking locations of sensors and imaging treatment probes during the performance of a treatment procedure.

BACKGROUND

When treating patients, clinicians often rely on patient data including X-ray data, computed tomography (CT) scan data, magnetic resonance imaging (MRI) data, or other imaging data that allows the clinician to view the internal anatomy of a patient. The clinician utilizes the patient data to identify targets of interest and to develop strategies for accessing the targets of interest for the surgical procedure.

The use of CT images as a diagnostic tool has become routine and CT results are frequently the primary source of information available to a clinician regarding the size and location of a lesion, tumor or other similar target of interest. This information is used by the clinician for planning a procedure such as a biopsy or an ablation procedure, but is only available as "offline" information which must typically be memorized to the best of the clinician's ability prior to beginning a procedure. A clinician reviews the CT image data slice by slice from each direction when attempting to identify or locate a target for navigation and treatment procedures. These methods however do not enable a clinician to effectively track the treatment probe through and inside of a patient's body and perform a surgical procedure.

SUMMARY

Systems and methods for tracking and treatment procedures are provided.

According to an embodiment of the present disclosure, a system includes a treatment probe, a first tracking sensor configured to track a location of the treatment probe, an ultrasound imager, a second tracking sensor configured to track a location of the ultrasound imager, and a tracking system. The ultrasound imager generates real-time ultrasound images. The tracking system receives location information from the first and second tracking sensors, tracks the location of the treatment probe and the location of the ultrasound imager, and displays the real-time ultrasound images and a representation of the treatment probe in one or more pre-stored images.

In an aspect, the system iteratively updates the displayed real-time ultrasound images and representation of the treatment probe as the treatment probe navigates.

In another aspect, the first and second tracking sensors are EM sensors. The first and second tracking sensors sense strength of an EM field.

In yet another aspect, the ultrasound imager further includes a sensor mount configured to receive the second tracking sensor thereon and mechanically engage with the ultrasound imager. The sensor mount engages a distal portion of the ultrasound imager. In an aspect, the sensor mount is a clip-on. The sensor mount is a sterile sleeve with rubber bands configured to fasten the sterile sleeve to the ultrasound transducer.

In another aspect, the sensor mount is a hypotube clip, which includes fingers to grab and lock the ultrasound imager. The hypotube clip includes a distal cap to cover the distal tip of the ultrasound imager. In yet another aspect, the sensor mount is a symmetrical hypotube clip, which locks the ultrasound imager in a circumferential direction.

In yet still another aspect, the system further includes a cannula configured to hold the ultrasound imager. The cannula includes a collet, for example a John Guest® collet, to lock the ultrasound imager. In an aspect, the cannula includes an O-ring type lock, which locks the ultrasound imager by rotating the O-ring type lock about the longitudinal axis of the ultrasound imager.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which:

FIGS. 4A-4G are graphical representations illustrating various sensor mounts for the ultrasound imager 140 of FIG. 1 in accordance with embodiments of the present disclosure;

DETAILED DESCRIPTION

The present disclosure provides a system for tracking a treatment probe and imaging both the treatment probe and a region of interest in a patient. While performing a surgical treatment, it is important to know exactly where a treatment probe is located within the patient's body, and the location with respect to a target for treatment. In addition, it is beneficial to see an actual image of the treatment probe as it is traversing tissue or entering the target. In this regard, the present disclosure describes location tracking features with which the spatial relationship between the treatment probe and the imaging device can be identified and presented as the treatment probe is navigated to a location within the patient in combination with real-time images of the treatment probe and the target as well as surrounding tissue.

A treatment plan may be used as a guide during the performance of the surgical procedure, where the system is configured to track the position of treatment probe inside the patient and give the clinician a real-time indication of the position of the treatment probe in relation to the target and the pre-planned pathway toward the target. The system also presents a clinician with the capability to compare and contrast pre-operative and post-operative CT image data to assess the outcome of a surgical treatment procedure that has been performed.

Although the present disclosure will be described in terms of specific illustrative embodiments, it will be readily apparent to those skilled in this art that various modifications, rearrangements and substitutions may be made without departing from the spirit of the present disclosure. The scope of the present disclosure is defined by the claims appended hereto.

A procedure according to the present disclosure, such as a microwave ablation procedure is generally divided into two phases: (1) a planning phase, and (2) a treatment phase. The planning phase of a procedure, such as microwave ablation treatment, is more fully described in provisional patent application No. 62/035,851 entitled TREATMENT PROCEDURE PLANNING SYSTEM AND METHOD, filed on Aug. 11, 2014 by Bharadwaj et al., the contents of which is hereby incorporated by reference in its entirety. An alternative planning or additional planning phase as well as a treatment phase is more fully described below.

A tracking and treatment system according to the present disclosure may be a unitary system configured to perform both the planning phase and the treatment phase, or the system may include separate devices and software programs for the various phases. An example of the latter may be a system wherein a first computing device with one or more specialized software programs is used during the planning phase, and a second computing device with one or more specialized software programs may import data from the first computing device to be used during the treatment phase.

Figure 1:
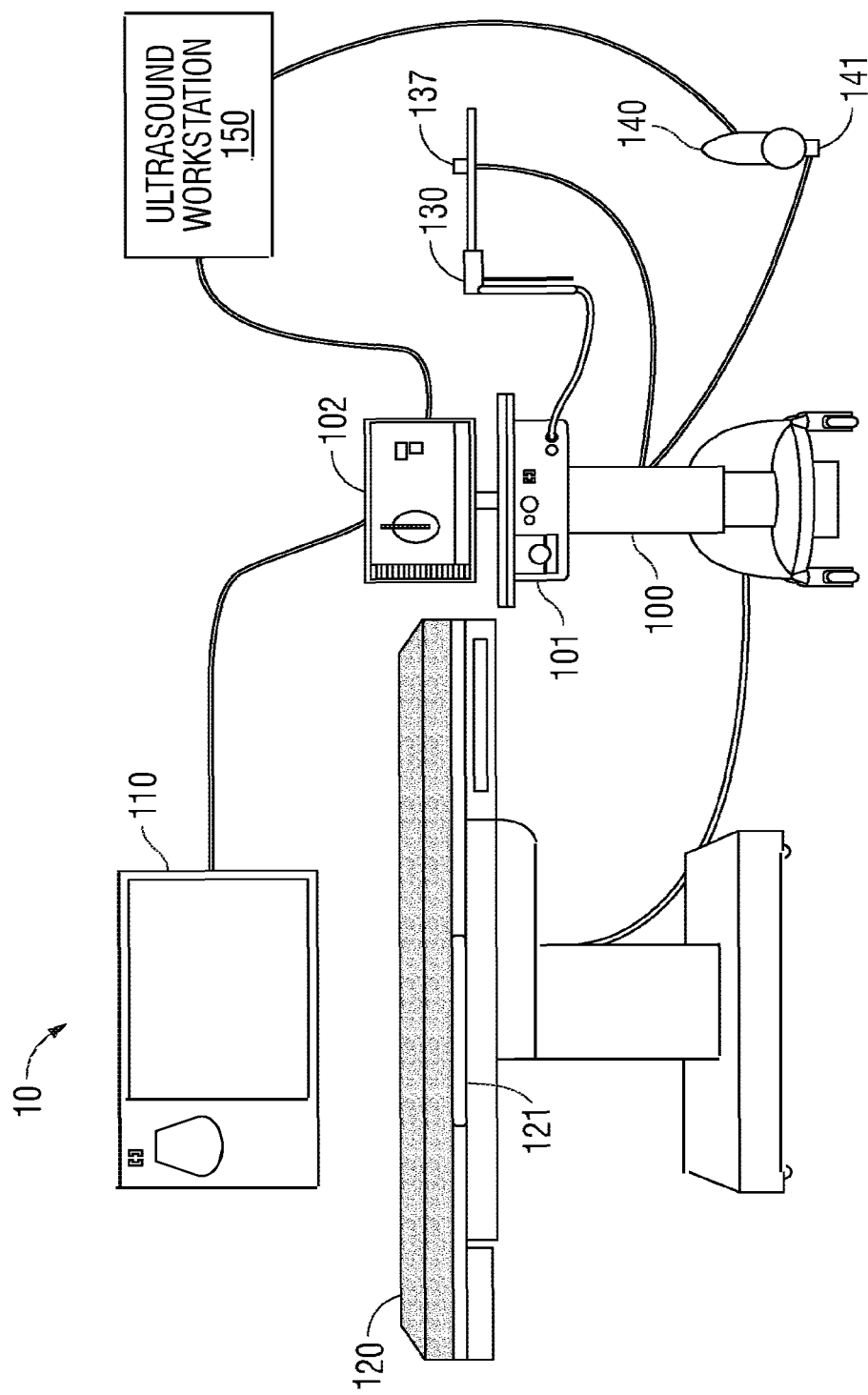
FIG. 1 is a schematic diagram of tracking and treatment system in accordance with an illustrative embodiment of the present disclosure.

Referring now to FIG. 1, the present disclosure is generally directed to a treatment system 10, which includes an EM tracking system 100, an electrosurgical generator 101, a workstation 102, a display 110, a table 120, a treatment probe 130, an ultrasound imager 140, and an ultrasound workstation 150. The EM tracking system 100 may be, for example, a laptop computer, desktop computer, tablet computer, or other similar device. The workstation 102 may also be used to control a cooling pump or other peripheral devices not expressly shown in FIG. 1. The EM tracking system 100 may interact with an EM field generator 121, one or more tracking sensors 137 and 141 (e.g., an EM sensor, though others could be used), and a display 110 on which a user interface presents the location of the tracking sensors 137 in the EM field in combination with one or more imaging modalities, as will be described in greater detail below. The workstation 102 includes software which converts signals received from the EM sensors 137 and 141 and performs necessary calculations to track the location of the EM sensors in an EM field. In addition to tracking information, the display 110 presents to a user the results of the software processing including instructions, images, and messages relating to the performance of the procedure. The EM field generator 121 rests on or may be built into a table 120 and is located under a patient thus generating an EM field around a portion of the patient through which navigation to a target is desired. Typically this will be the patient's torso which enables navigation to and treatment of all the major organs of the body. However, the same system could be used to treat other locations on the patient. An example of such an EM field generator 121 is the AURORA™ system sold by Northern Digital Inc.

The electrosurgical generator 101 generates electrosurgical energy (e.g., RF or microwave) and provides the generated energy to the treatment probe 130. The treatment probe 130 is a surgical instrument, for example, a microwave ablation antenna used to ablate and treat tissue. Various other surgical instruments or surgical tools, such as electrosurgical pencils, vessel sealers, staplers, resection devices and others, may also be used with EM tracking system 100 either with or without an EM sensor 137. In one embodiment, located on the treatment probe 130 is the tracking sensor 137 as will be described in detail below, allowing for the tracking of the location of the treatment probe 130 in the EM field. While the present disclosure describes the use of the system 10 in a surgical environment, it is also envisioned that some or all of the components of system 10 may be used in alternative settings, for example, at a treatment review board or other office setting such as during a post treatment review of the procedure or assessment of progress of the patient.

In addition to the EM tracking system 100, the system 10 includes the capabilities for patient, target, and treatment probe 130 visualization using ultrasonic imaging. The ultrasound imager 140, such as an ultrasonic wand, may be used to image the patient's body during the procedure to visualize the location of the surgical instruments, such as the treatment probe 130, inside the patient's body. The ultrasound imager 140 may also have an EM tracking sensor 141 embedded within or attached to the ultrasonic wand, for example, a clip-on sensor or a sticker sensor. As described further below, the ultrasound imager 140 may be positioned in relation to the treatment probe 130 such that the treatment probe 130 is at an angle to the ultrasound image plane, thereby enabling the clinician to visualize the spatial relationship of the treatment probe 130 with the ultrasound image plane and with objects being imaged. Further, the EM tracking system 100 may also track the location of ultrasound imager 140 using the EM sensor 141 placed thereon.

The ultrasound imager 140 includes an ultrasound transducer (140a in FIG. 4A) which emits ultrasound energy receives reflected ultrasound energy. The ultrasound imager 140 then transmits reflected ultrasound waves to the ultrasound workstation 150, which processes the reflected ultrasound waves and generates ultrasound images.

The treatment probe 130 may be an ablation probe used to ablate a lesion or tumor (hereinafter referred to as a "target") by using electromagnetic radiation or microwave energy to heat tissue in order to denature or kill cancerous cells. The construction and use of a system including such an ablation probe is more fully described in provisional patent application No. 62/041,773 entitled MICROWAVE ABLATION SYSTEM, filed on Aug. 26, 2014, by Dickhans, co-pending patent application Ser. No. 13/836,203 entitled MICROWAVE ABLATION CATHETER AND METHOD OF UTILIZING THE SAME, filed on Mar. 15, 2013, by Ladtkow et al., and co-pending patent application Ser. No. 13/834,581 entitled MICROWAVE ENERGY-DELIVERY DEVICE AND SYSTEM, filed on Mar. 15, 2013, by Brannan et al., the contents of all of which are hereby incorporated by reference in its entirety.

As described above, the location of the treatment probe 130 within the body of the patient may be tracked during the surgical procedure using the EM tracking system 101 and the EM sensor 137 located on the treatment probe 130. Various types of sensors may be used, such as a printed sensor, the construction and use of which is more fully described in provision patent application No. 62/095,563 entitled MEDICAL INSTRUMENT WITH SENSOR FOR USE IN A SYSTEM AND METHOD FOR ELECTROMAGNETIC NAVIGATION, filed Dec. 22, 2014, the entire contents of which is incorporated herein by reference. Prior to starting the procedure, the clinician is able to verify the accuracy of the tracking system.

The workstation 102 may combine the ultrasound images from the ultrasound workstation 150 and EM data from the EM tracking system 100. The EM data may include spatial relationship between the location of the ultrasound imager 140 and the location of the treatment probe 130 in the EM field. Based on the spatial relationship, the workstation 102 generates images depicting the location of the treatment probe 130 with respect to pre-stored images illustrating the treatment probe 130 on display 110. In addition the workstation 102 generates a representation of the location of the treatment probe in relation to the ultrasound images such that the treatment probe 130 is depicted with respect to the ultrasound image and any pre-planned pathway to a target in the ultrasound image is also displayed allowing the clinician to follow the pathway and achieve the target.

Figure 2:
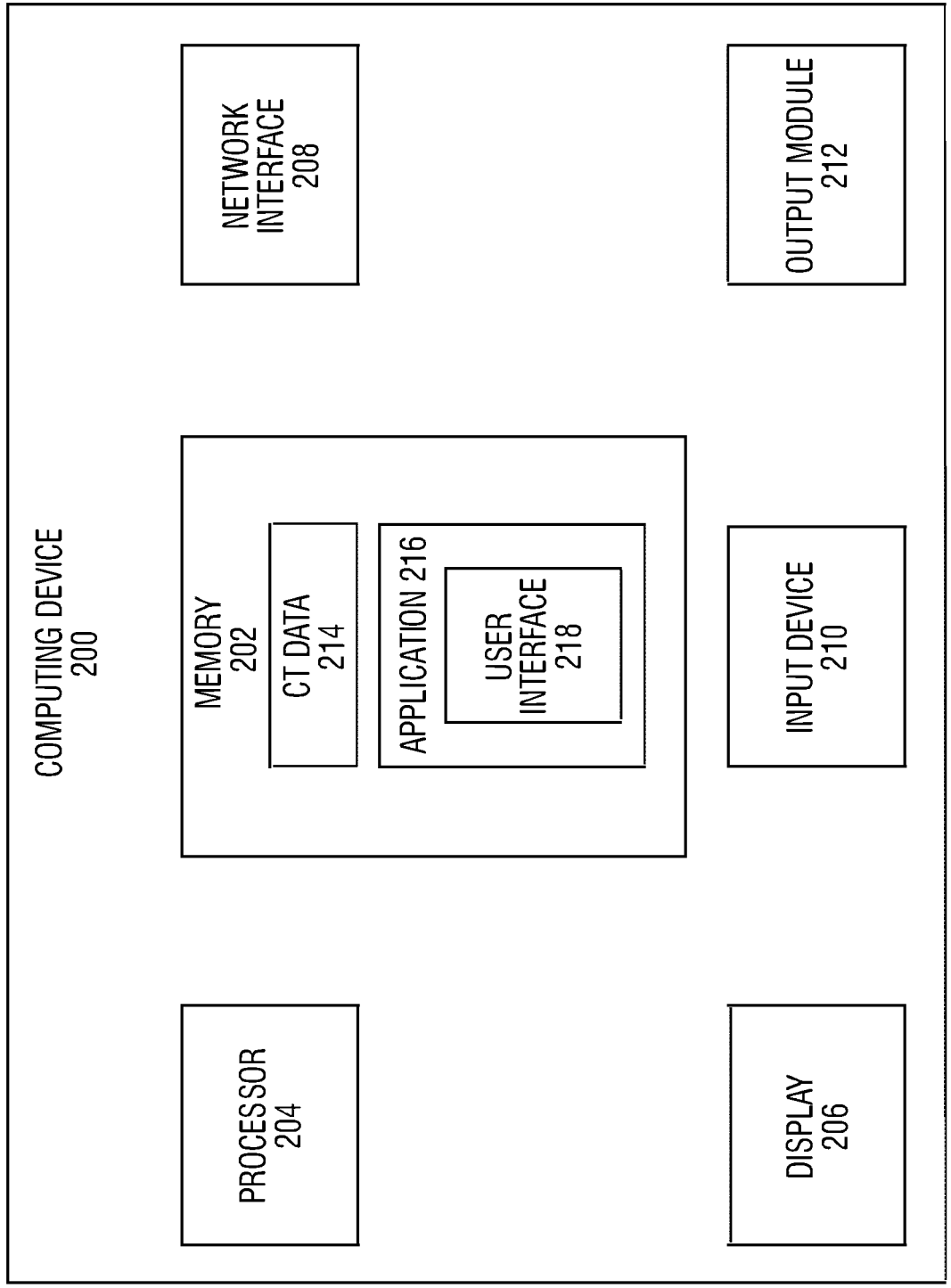
FIG. 2 is a schematic diagram of a computing device which forms part of the tracking and treatment system 10 of FIG. 1 in accordance with an embodiment of the present disclosure.

Turning now to FIG. 2, there is shown a system diagram of a computing device, which can be the EM tracking system 100, the workstation 102, or the ultrasound workstation 150. The computing device 200 may include memory 202, processor 204, the display 206, network interface 208, input device 210, and/or output module 212.

Memory 202 includes any non-transitory computer-readable storage media for storing data and/or software that is executable by processor 204 and which controls the operation of the computing device 200. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 200.

Memory 202 may store application 216 and/or CT data 214. Application 216 may, when executed by processor 204, cause the display 206 to present user interface 218.

Processor 204 may be a general purpose processor, a specialized graphics processing unit (GPU) configured to perform specific graphics processing tasks while freeing up the general purpose processor to perform other tasks, and/or any number or combination of such processors.

The display 206 may be touch-sensitive and/or voice-activated, enabling the display 206 to serve as both an input and output device. Alternatively, a keyboard (not shown), mouse (not shown), or other data input devices may be employed.

Network interface 208 may be configured to connect to a network such as a local area network (LAN) consisting of a wired network and/or a wireless network, a wide area network (WAN), a wireless mobile network, a Bluetooth network, and/or the internet. For example, the computing device 200 may receive computed tomographic (CT) image data of a patient from a server, for example, a hospital server, internet server, or other similar servers, for use during surgical ablation planning. Patient CT image data may also be provided to the computing device 200 via a removable memory 202. The computing device 200 may receive updates to its software, for example, application 216, via network interface 208. The computing device 200 may also display notifications on the display 206 that a software update is available.

Input device 210 may be any device by means of which a user may interact with the computing device 200, such as, for example, a mouse, keyboard, foot pedal, touch screen, and/or voice interface.

Output module 212 may include any connectivity port or bus, such as, for example, parallel ports, serial ports, universal serial busses (USB), or any other similar connectivity port known to those skilled in the art.

Application 216 may be one or more software programs stored in memory 202 and executed by processor 204 of the computing device 200. During a planning phase, application 216 guides a clinician through a series of steps to identify a target, size the target, size a treatment zone, and/or determine an access route to the target for later use during the procedure phase. In some embodiments, application 216 is loaded on computing devices in an operating room or other facility where surgical procedures are performed, and is used as a plan or map to guide a clinician performing a surgical procedure, but without any feedback from the treatment probe 130 used in the procedure to indicate where the treatment probe 130 is located in relation to the plan Application 216 may be installed directly on the computing device 200, or may be installed on another computer, for example a central server, and opened on the computing device 200 via network interface 208. Application 216 may run natively on the computing device 200, as a web-based application, or any other format known to those skilled in the art. In some embodiments, application 216 will be a single software program having all of the features and functionality described in the present disclosure. In other embodiments, application 216 may be two or more distinct software programs providing various parts of these features and functionality. For example, application 216 may include one software program for use during the planning phase, and a second software program for use during the treatment phase. In such instances, the various software programs forming part of application 216 may be enabled to communicate with each other and/or import and export various settings and parameters relating to the navigation and treatment and/or the patient to share information. For example, a treatment plan and any of its components generated by one software program during the planning phase may be stored and exported to be used by a second software program during the procedure phase.

Application 216 communicates with a user interface 218 which generates a user interface for presenting visual interactive features to a clinician, for example, on the display 206 and for receiving clinician input, for example, via a user input device. For example, user interface 218 may generate a graphical user interface (GUI) and output the GUI to the display 206 for viewing by a clinician.

The computing device 200 may be linked to the display 110, thus enabling the computing device 200 to control the output on the display 110 along with the output on the display 206. The computing device 200 may control the display 110 to display output which is the same as or similar to the output displayed on the display 206. For example, the output on the display 206 may be mirrored on the display 110. Alternatively, the computing device 200 may control the display 110 to display different output from that displayed on the display 206. For example, the display 110 may be controlled to display guidance images and information during the surgical procedure, while the display 206 is controlled to display other output, such as configuration or status information of an electrosurgical generator 101 as shown in FIG. 1.

As used herein, the term "clinician" refers to any medical professional (i.e., doctor, surgeon, nurse, or the like) or other user of the system 10 involved in performing, monitoring, and/or supervising a medical procedure involving the use of the embodiments described herein.

Figure 3A:
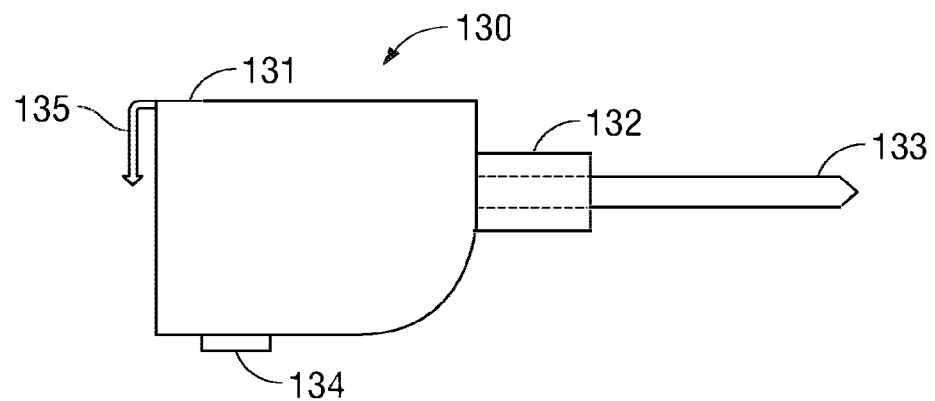
FIGS. 3A and 3B are graphical representations illustrating the treatment probe 130 of FIG. 1 in accordance with embodiments of the present disclosure.
Figure 3B:
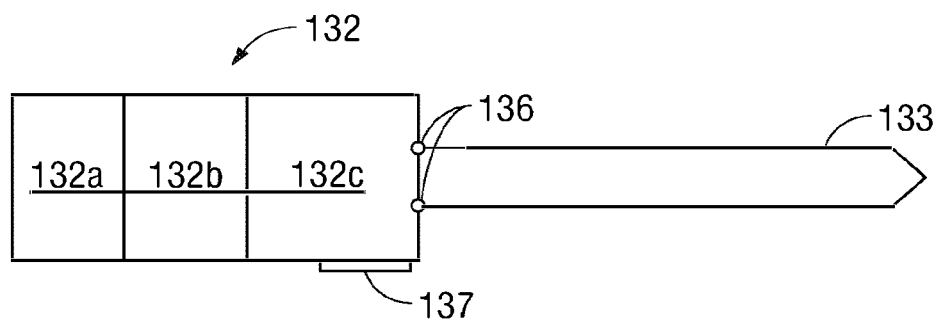

Due to potential interferences both electrical and mechanical, it is not always desirable or possible to place the EM tracking sensor 137 on the distal tip of a treatment probe 130. Thus, for example in the case of a microwave ablation probe, it is necessary to place the EM tracking sensor 137 some distance proximal the distal end of the microwave ablation probe. However because treatment occurs at and near the distal end of a microwave ablation probe it is important to know its location in space and more particularly the patient. When the spatial relationship between the EM tracking sensor 137 and the tip of the shaft 133 is known, the location of the tip of the shaft 133 can be identified based on the spatial relationship. FIGS. 3A and 3B provide one solution for addressing this issue without the need to alter an existing treatment probe 130.

FIG. 3A depicts a hub 131 which can be placed around existing treatment probes, such as the Emprint™ ablation probe currently sold by Medtronic PLC, in order to secure the EM tracking sensors 137 and to enable the use of such a device in an EM field of the system 10. The hub 131 includes a cannula 132 and first and second locking member 134 and 135, respectively. As shown in FIG. 3A, a portion of the shaft 133 of the treatment probe 130 extends beyond the distal end of the hub 131 allowing for effective use of the treatment probe 130. The treatment probe 130 is secured in the hub 131 by the cannula 132, the first locking member 134, which prevents the axial movements of the treatment probe 130, and the second locking member 135 prevents rotational movement of the treatment probe 130, relative to the hub 131. The first and second locking members 134 and 135 may be clip-type locks or any locking devices suitable to lock movements of the treatment probe 130 relative to the hub 131.

Turning now to FIG. 3B, there is shown an expanded view of the cannula 132 of the hub 131 with the shaft 133 of the treatment probe 130 extending therefrom. As depicted in FIG. 3B, the cannula 132 has three parts, a proximal part 132a, a middle part 132b, and a distal part 132c. In one embodiment the proximal part 132a and the distal part 132c are rigid and the middle part 132b is flexible. The flexible middle part 132b helps eliminate any stress that the hub 131 might place on the shaft 133 of the treatment probe 130. As an example, the hub 131 may be made of a less flexible material than the shaft 133 of the treatment probe, thus when placed in the hub 131 normal operation of the treatment probe 130 might induce stresses in the shaft 133 at the locations identified as 136 in FIG. 3B. By adding the flexible middle part 132b, these stresses are reduced and the potential for damaging the treatment probe 130 is also reduced.

As shown in FIG. 3B, an EM tracking sensor 137 is affixed at the distal part 132c of the cannula 132. In one embodiment, by being placed in the EM field, the EM tracking sensor 137 outputs a voltage (or multiple voltages) that can be sensed by the EM tracking system 100 and converted into location information of the EM tracking sensor 137 in the EM field generated by the EM field generator 121 to identify the location of the EM tracking sensor 137 or the distal part 132c within an EM field, and therewith the location of the EM tracking sensor 137 with respect to the patient. By knowing the distance from the EM tracking sensor 137 to the distal end of the treatment probe 130, one or more of the software applications running on the EM tracking system 100 determine the location of the distal end of the treatment probe 130, and generate a representation of its location on the display based on the sensed location of the EM tracking sensor 137. This representation can be used to assist in navigating to a desired point in the patient as depicted in either two-dimensional images or a three-dimensional model of a desired portion of the patient. For example, the system 10 may display a virtual image of the shaft 133 overlaid over an ultrasound image on the display 110.

Since the only middle part 132b of the cannula 132 is flexible, when the shaft 133 navigates within a patient's body, the distal part 132c including the EM tracking sensor 137 moves along with the navigation of the shaft 133. Thus, flexibility of the middle part 132b also increases detection accuracy of the current location of the shaft 133 and prevent the shaft 133 from breaking due to the stress. The EM tracking sensor 137 may be rigidly affixed by an adhesive or by other suitable means which do not interfere with the EM field and the frequency employed by the treatment probe 130, may be used. Alternatively, the EM tracking sensor 137 may be printed on the cannula 132 at a predetermined position.

Figure 4A:
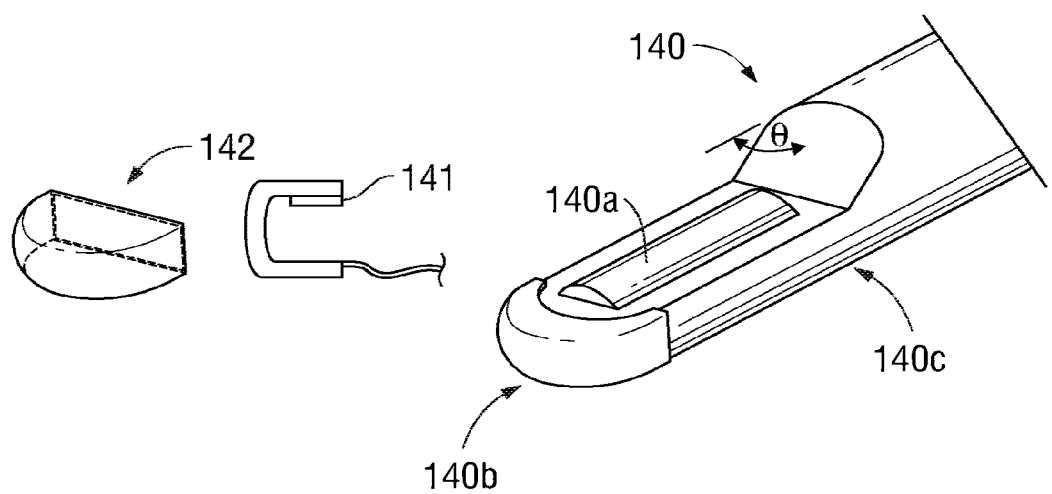

Now turning to FIGS. 4A-4G, there are shown various sensor mounts for the ultrasound imager 140 to provide location information about the ultrasound imager 140 to the EM tracking system 100 to provide real time images of the patient while the clinician navigates the treatment probe 130 to a desired location. These sensor mounts are to enable the use of off the shelf ultrasound probes with the system 10, thus enabling clinicians to utilize their preferred imaging systems and probes and integrate them into system 10. In particular, FIG. 4A shows the ultrasound imager 140, an EM tracking sensor 141, and a sensor mount 142. The ultrasound imager 140 includes an ultrasound transducer 140a which emits ultrasound energy and receives reflected ultrasound energy. The received ultrasound energy is then transmitted to an image processing device such as the ultrasound workstation 150, which calculates and processes the reflected ultrasound energy to generate real-time ultrasound images and transmits to the workstation 102. When the ultrasound imager 140 is proximate the treatment probe 130 the images may include the shaft 133, a target region for treatment, and other internal organs. The processed real-time images are displayed on the display 110.

The ultrasound imager 140 may include a smooth round-shape at its distal tip 140b and/or a cut-out portion 140c in the middle thereof. The cut-out portion 140c may have an inclination from the top surface toward the center. The inclination has an angle θ with respect to the longitudinal axis, which is greater than zero degrees and less than 90 degrees.

The EM tracking sensor 141 is mounted inside of a sensor mount 142 which may slidably and releasably engage with the distal tip 140b. The sensor mount 142 includes a locking mechanism, which will be described below in FIGS. 4E-4H. The locking mechanism makes a locking engagement sufficiently strong enough so that the ultrasound imager 140 can navigate inside of the patient's body without risks of removal of the sensor mount 142. The material of the sensor mount 142 should not hinder propagation and reception of the ultrasound energy by the ultrasound transducer 140a.

The position of the EM tracking sensor 141 may be predetermined to have a spatial relationship between the EM tracking sensor 141 and the distal tip 140b of the ultrasound imager 140. As with the treatment probe 130, described above the EM tracking system 100 is able to identify the location of the distal tip 140b based on the spatial relationship and the detected location of the EM tracking sensor 141. In this manner, the location of the ultrasound imager 140 in space, and more particularly within or over the patient, can be determined such that the ultrasound image plane generated by the ultrasound imager 140 can be determined, compared, and correlated to the location of the treatment probe 130.

In another aspect, the material of the sensor mount 142 may not hinder propagation and reception of the ultrasonic waves by the ultrasound transducer 140a.

Figure 4B:
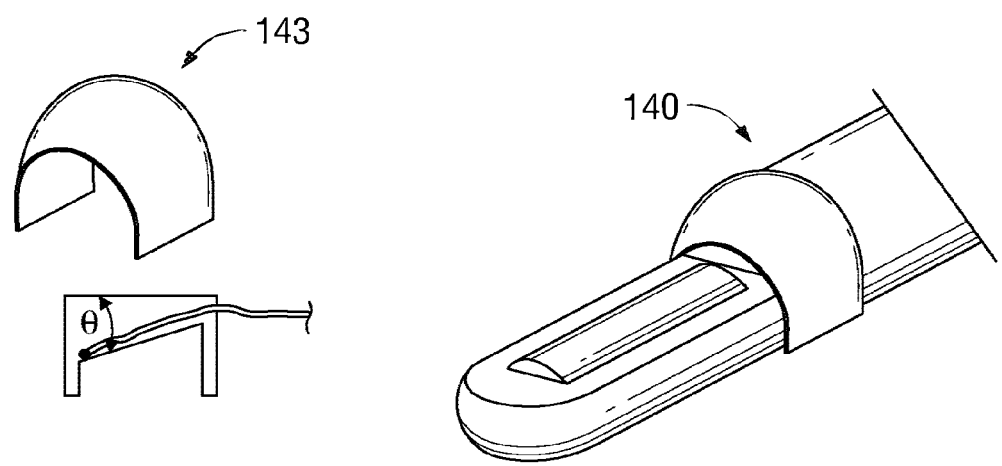

In FIG. 4B, there is shown a sensor mount 143, which is a top cap version. The sensor mount 143 engages with the ultrasound imager 140 from the top or at the inclination of the ultrasound imager 140. Since the inclination has the angle θ, the top portion of the sensor mount 143 also has an inclination having the angle θ with respect to the longitudinal axis of the ultrasound transducer 140a, they fit to each other. Also, the inclinations of the sensor mount 143 and the cut-out portion 140c make possible to align the EM tracking sensor 141 with an angle with which the ultrasound imager 140 transmits ultrasonic waves. In an aspect, the position in the sensor mount 143, to which the EM tracking sensor 141 is fixed, may be predetermined to set a spatial relationship between the EM tracking sensor 141 and the ultrasound transducer 140a. It will be appreciated by those of skill in the art that extending from the sensor mounts 142 and 143 are wires which are used to connect the EM tracking sensor 141 to the EM tracking system 100 such that the location of the EM tracking sensor 141 in the EM field can be determined.

Figure 4C:
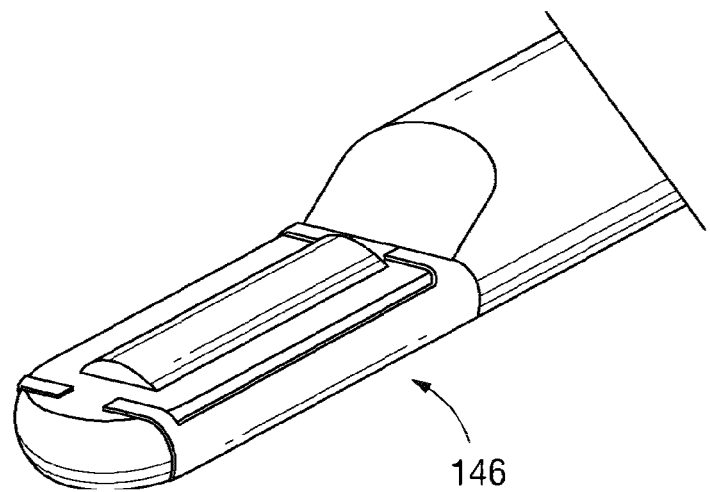
Figure 4D:
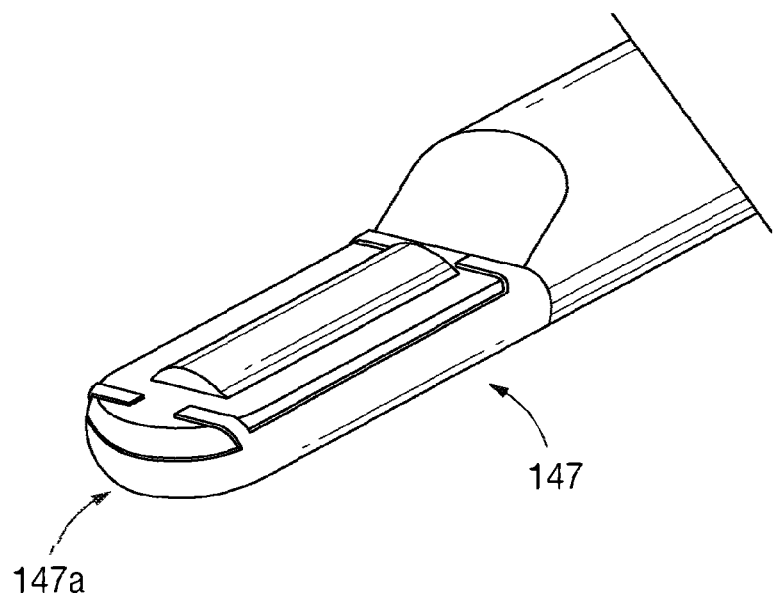

Turning now to FIGS. 4C and 4D, there are shown sensor mounts, which are hypotubes. In FIG. 4C, the hypotube 146 as a sensor mount may have four fingers that grab the cut-out portion 140c (FIG. 4A) of the ultrasound imager 140 and may cover a portion of the bottom and the side of the ultrasound imager 140. The EM tracking sensor 141 may be between the hypotube 146 and the ultrasound imager 140, or may be affixed at a predetermined position on the outside surface of the hypotube 146. The hypotube 146 is made of materials, which decreases neither the sensitivity of the EM tracking sensor 141 in the EM field nor the quality of ultrasound images obtained by the ultrasound transducer 140a.

The hypotube 147 of FIG. 4D includes all the features of the hypotube 146 of FIG. 4C and further includes a distal cap 147a covering a portion of the distal tip 140b of the ultrasound imager 140.

Turning now to FIGS. 4E-4G, there are shown sensor mounts, which are hypotube clips. FIG. 4E shows a perspective view and FIG. 4F shows a transverse view of the ultrasound imager 140. The hypotube clip 148 may be connected with the ultrasound imager 140 from the side of the ultrasound transducer 140a. The hypotube clip 148 may include two clip tabs, which are bent flat to match the profile of the ultrasound transducer 140a. The EM tracking sensor 141 may be affixed at a predetermined position on the hypotube clip 148. In an aspect, the clip tabs 148a may lock the EM tracking sensor 141 in the circumferential direction.

The hypotube clip 149 of FIG. 4G includes only one clip tab 149a at the proximal end of the ultrasound transducer 140a and a cap 149b at the distal end of the ultrasound transducer 140a which covers the distal tip 140b. In an aspect, the cap 149b may embed the EM tracking sensor 141. The clip tab 194a and the cap 149b together may prevent a shift movement along the longitudinal direction so that the position of the EM tracking sensor 141 can be consistent with respect to the distal tip of the ultrasound imager 140.

As will be appreciated, one of the issues with connecting the EM tracking sensor 141 to the ultrasound imager 140 is to ensure that the EM tracking sensor 141 does not interfere with the ultrasound transducer 140a. Accordingly, all the preceding embodiments focused on placing the EM tracking sensor 141 near the ultrasound transducer 140a but not on the ultrasound transducer 140a. An alternative approach would be to adhere the EM tracking sensor 141 to the ultrasound transducer 140a using a phantom material, which does not interfere with the transducer's imaging capabilities.

Figure 5A:
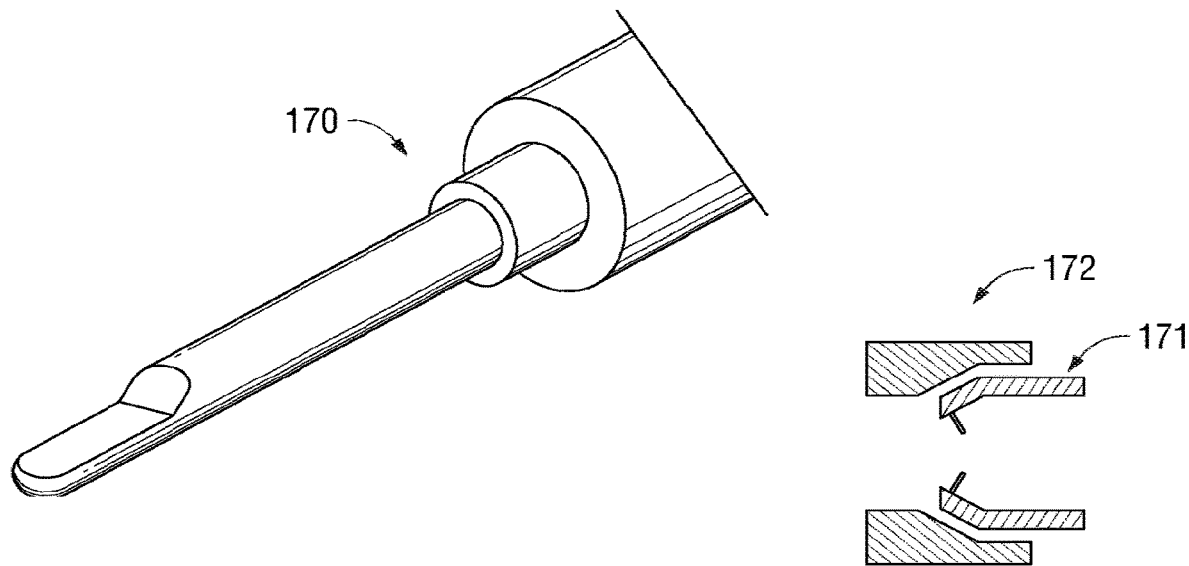
FIGS. 5A-5C are graphical representations illustrating locking mechanisms for the ultrasound imager 140 of FIG. 1 in accordance with embodiments of the present disclosure.

A further approach, much like discussed above, with respect to the treatment probe 130, is to insert the ultrasound imager 140 into a cannula 170 which includes the EM tracking sensor 141. By fixing the orientation of the cannula 170 to the ultrasound imager 140, the effect is similar to that of affixing the EM tracking sensor 141 directly to the ultrasound imager 140. In FIG. 5A, there is shown a locking mechanism for connecting the ultrasound imager 140 to a cannula 170. The shaft of an ultrasound imager 140 can be locked into the cannula 170 using a collet, for example a John Guest® collet, which includes an inner tube 171 and an outer tube 172. When the ultrasound imager 140 is inserted into the cannula 170, the outer tube 172 compresses the inner tube 171. As a result, the teeth of the inner tube 171 grab the ultrasound imager 140 holding it in place with respect to the cannula 170.

Figure 5B:
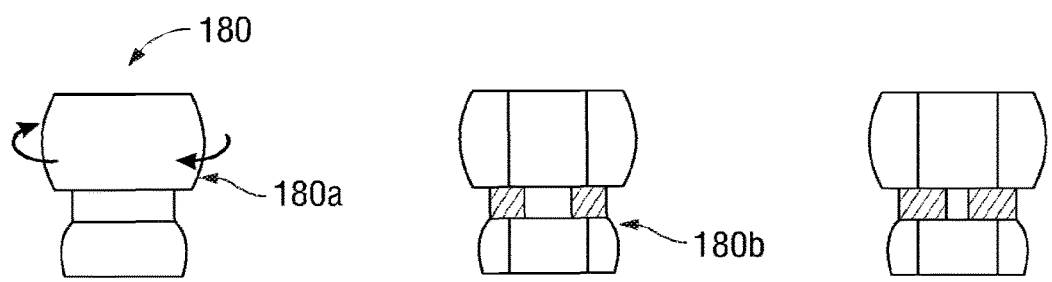

An alternative approach is shown in FIG. 5B, there is shown a Tuohy-Borst type locking mechanism 180 which can be used to lock a cannula 170 to the ultrasound imager 140 using an O-ring. The locking mechanism 180 includes a front end 180a and an O-ring 180b. In operation the locking mechanism is locate on a proximal end of a cannula 170 and the ultrasound imager is inserted into the cannula and locked into place by rotating the front end 180a such that the O-ring type is compressed locking the cannula 170 to the ultrasound imager 140. Rotation of the front end 180a in the opposite direction releases the pressure applied by the O-ring to the ultrasound imager 140 and allows for its removal from the cannula 170.

Figure 5C:
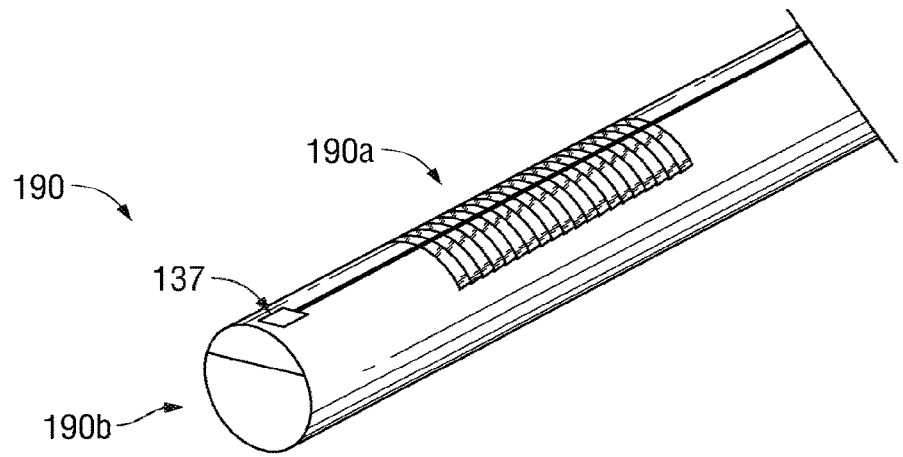

Now turning to FIG. 5C, there is shown a cannula 190 into which the ultrasound imager 140 may be inserted. The cannula 190 may include a flexible middle portion 190a, which in combination with a D-shape 190*b* at the distal end allows for the ultrasound imager 140 to self-align in the cannula 190 and have flexibility of motion. In addition, the D-shape 190*b* allows for the accommodation of a 4-way ultrasound transducer. The EM sensor 137 may be formed directly on the cannula 190. As a result of the self-alignment enabled by the D-shape, the orientation of the EM sensor 137 and the ultrasound imager 140 placed therein (and not shown in FIG. 5C) is fixed, even in instances where the ultrasound imager flexes or bends, such as when the ultrasound imager 140 is a 4-way ultrasound imager. The EM sensor 137 may be connected via a wire to the EM tracking system 100 as shown in FIG. 1. The wire may run internally or externally of the cannula 190, and may be modified to accommodate the flexure of the cannula 190.

In addition to the foregoing, methods for performing a treatment (e.g., microwave ablation) procedure using the EM tracking sensor 137 of the treatment probe 130 and ultrasound imager 140 are further described in provisional patent application No. 62/154,958 entitled SYSTEMS AND METHODS FOR CONTROLLING AN ELECTROSURGICAL GENERATOR DURING A MICROWAVE ABLATION PROCEDURE, filed on Apr. 30, 2015, by Covidien LP, the contents of which is hereby incorporated by reference in its entirety.

Figure 6:
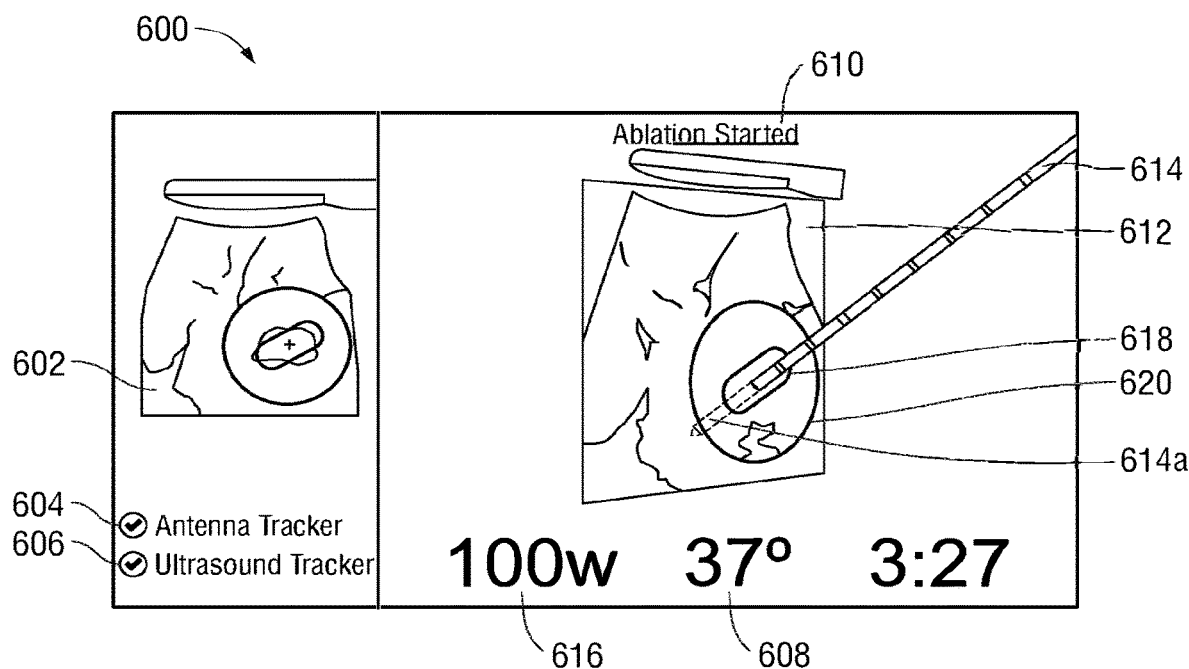
FIG. 6 is a graphical representation of an image displayed on the display 110 of FIG. 1 in accordance with embodiments of the present disclosure.

FIG. 6 shows a graphical interface 600 displayed on the display 110 of FIG. 1. The display 110 displays an ultrasound image 602, the left side image, received from the ultrasound workstation 150 and also shows two indications 604 and 606 informing that an antenna tracker and an ultrasound tracker are activated and being tracked. Right side image 612 is a composite of image 600 illustrating the progression of a treatment, here microwave ablation. Indication 610 may shows that an ablation treatment has started. The treatment probe 130 is displayed as generated image 614, its location and orientation on the image having been determined by the special relationship between the treatment probe 130 and the ultrasound probe 140, as described above. A treatment region 618 shows the tissue which has been treated, while target region 620 depicts the entire region to be treated. The tip 614*a* of the treatment probe 130 is displayed being inserted to the target region. Other textual information 616 and 608 may be displayed to show power being applied to the treatment probe 130 and the temperature of the treatment probe 130 or tissue proximate the treatment probe 130.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A system, comprising:
   an ultrasound imager configured to image a patient during a medical procedure, the ultrasound imager defining a longitudinal axis and including a cut-out portion, a top surface extending along the cut-out portion, a bottom surface extending along the cut-out portion opposite the top surface, and an ultrasound sensor extending along the top surface, the ultrasound sensor configured to generate real-time ultrasound images orthogonal to the longitudinal axis; and
   a sensor mount having at least one clip tab configured to be mounted over at least a portion of the top surface to releasably attach the sensor mount to the cut-out portion.

2. The system according to claim 1, wherein at least a portion of the sensor mount is mounted over the bottom surface of the ultrasound imager.

3. The system according to claim 1, wherein the sensor mount includes a first pair of opposing clip tabs configured to be mounted over a first portion of the top surface disposed proximal to the ultrasound sensor and a second pair of opposing clip tabs configured to be mounted over a second portion of the top surface disposed distal to the ultrasound sensor.

4. The system according to claim 1, wherein the sensor mount includes a first clip tab configured to be releasably mounted over a first portion of the top surface disposed proximal to the ultrasound sensor and a second clip tab configured to be releasably mounted over a second portion of the top surface disposed distal to the ultrasound sensor.

5. The system according to claim 1, wherein the sensor mount includes a distal cap configured to be mounted over a distal end portion of the cut-out portion.

6. The system according to claim 1, wherein the sensor mount includes a single clip tab configured to be releasably mounted over a portion of the top surface disposed proximal to the ultrasound sensor.

7. The system according to claim 1, wherein the cut-out portion has an inclination relative to the longitudinal axis extending from the top surface.

8. The system according to claim 1, further comprising an electromagnetic (EM) tracking sensor configured to be disposed between the cut-out portion and the sensor mount for tracking a location of the ultrasound imager.

9. The system according to claim 8, wherein the EM tracking sensor is configured to be disposed between the top surface and an inner surface of the sensor mount.

10. The system according to claim 1, wherein the sensor mount is a hypotube clip.

11. The system according to claim 1, wherein the ultrasound imager is configured to be inserted into a body of the patient.

12. A system, comprising:
    an ultrasound imager configured to image a patient during a medical procedure, the ultrasound imager defining a longitudinal axis and including a top surface and an ultrasound sensor extending along the top surface, the ultrasound sensor configured to generate real-time ultrasound images orthogonal to the longitudinal axis; and
    a sensor mount having at least one clip tab configured to engage at least a portion of the top surface to releasably attach the sensor mount to the ultrasound imager.

13. The system according to claim 12, wherein at least a portion of the sensor mount is mounted over a bottom surface of the ultrasound imager.

14. The system according to claim 12, wherein the sensor mount includes a first pair of opposing clip tabs configured to be mounted over a first portion of the top surface disposed proximal to the ultrasound sensor and a second pair of opposing clip tabs configured to be mounted over a second portion of the top surface disposed distal to the ultrasound sensor.

15. The system according to claim 12, wherein the sensor mount includes a first clip tab configured to be releasably mounted over a first portion of the top surface disposed proximal to the ultrasound sensor and a second clip tab configured to be releasably mounted over a second portion of the top surface disposed distal to the ultrasound sensor.

16. The system according to claim 12, wherein the sensor mount includes a distal cap configured to be mounted over a distal end portion of the ultrasound imager distal to the ultrasound sensor.

17. The system according to claim 12, wherein the sensor mount includes a single clip tab configured to be releasably mounted over a portion of the top surface disposed proximal to the ultrasound sensor.

18. The system according to claim 12, further comprising an electromagnetic (EM) tracking sensor configured to be disposed between the top surface and the sensor mount for tracking a location of the ultrasound imager.

19. The system according to claim 12, wherein the ultrasound imager is configured to be inserted into a body of the patient.

20. A system, comprising:
- an ultrasound imager configured to image a patient during a medical procedure, the ultrasound imager having a cut-out portion including a top surface and an ultrasound sensor extending along the top surface, the ultrasound sensor configured to generate real-time ultrasound images; and
- a sensor mount having at least one clip tab configured to engage at least a portion of the top surface to releasably attach the sensor mount to the cut-out portion for coupling an electromagnetic (EM) sensor to the ultrasound imager.

* * * * *